United States Patent [19]

Bunce et al.

[11] 4,356,722

[45] Nov. 2, 1982

[54] APPARATUS FOR TESTING A LIQUID SAMPLE

[75] Inventors: Roger A. Bunce; John H. Kennedy; Larry J. Kricka, all of Birmingham; Thomas P. Whitehead, Leamington Spa, all of England

[73] Assignee: The Secretary of State for Social Services in Her Britannic Majesty's Government of the United Kingdom of Great Britain and Northern Ireland, London, England

[21] Appl. No.: 203,572

[22] Filed: Nov. 5, 1980

[30] Foreign Application Priority Data

Nov. 8, 1979 [GB] United Kingdom ................ 7938739

[51] Int. Cl.³ ............................................ G01N 35/00
[52] U.S. Cl. ........................................... 73/53; 422/68
[58] Field of Search ........... 73/863.11, 863.32, 864.23, 73/864.24, 53; 422/68

[56] References Cited

U.S. PATENT DOCUMENTS

| | | | |
|---|---|---|---|
| 3,536,449 | 10/1970 | Astle | 73/863.32 |
| 3,873,316 | 3/1975 | McKie | 422/68 |
| 3,902,371 | 9/1975 | Hooper | 73/864.24 |
| 4,058,370 | 11/1977 | Suovaniemi | 73/863.32 |
| 4,234,316 | 11/1980 | Hevey | 422/68 |
| 4,258,761 | 3/1981 | Bennett, Jr. | 73/863.32 |

OTHER PUBLICATIONS

Clinical Chemistry 25, No. 1, 1979, Yoshioka et al., pp. 35–38.
Experientia, 36, 1980, Hoshi et al., p. 1122.
Protides of Biological Fluids, 24th Colloquium 1976, Ruitenberg & VanKnapen, pp. 771–774.
Immunological Methods, 31 (1979), Carlier, Bout & Capron, pp. 237–246.
Abbott Diagnostics (Trade Publication) Immunoassay for Hepatitis B.

*Primary Examiner*—S. Clement Swisher
*Attorney, Agent, or Firm*—Cushman, Darby & Cushman

[57] ABSTRACT

Apparatus for testing at least one liquid sample, by immersion therein of a probe for coaction between said probe and sample, having a reloadable sample carrier for at least one sample container; a reloadable probe carrier for at least one probe; a frame having locating means for relatively locating the sample carrier and the probe carrier laterally in the frame, parallel motion means for guiding the probe longitudinally into the sample container and stop means for locating the probe at a predetermined distance into the sample container, locking means preventing the probe from being withdrawn more than a predetermined distance in the outward direction from the sample container, timing and control means for releasing said locking means after a predetermined time, and self acting withdrawal means for withdrawing the probe and probe carrier to a position clear of the sample container; the said sample carrier and probe carrier being arranged so as to be severally removable away from the said frame.

15 Claims, 5 Drawing Figures

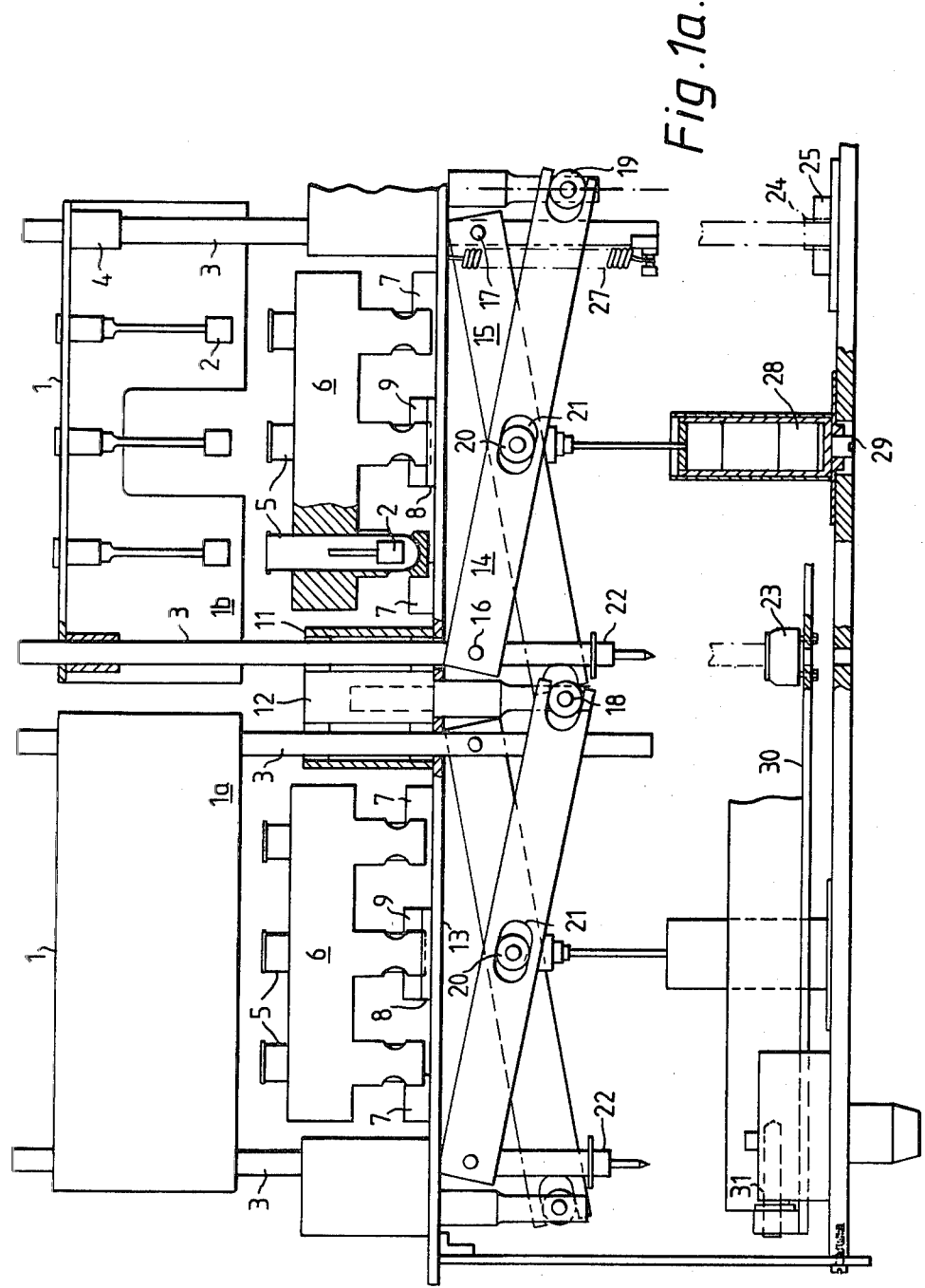

APPARATUS FOR TESTING A LIQUID SAMPLE

BACKGROUND AND SUMMARY OF THE INVENTION

This invention relates to apparatus for testing a liquid sample by immersion therein of a probe for coaction therebetween. The said coaction may be of a chemical or of a physical nature.

Certain chemicals can be adsorbed or covalently bonded to a plastics substance such as polystyrene, and yet be able to enter into other chemical reactions. An example of such a chemical is the globulin fraction of antiserum against alpha-feto protein. In this particular example the fact is used for the determination of the concentration of alpha-feto protein in human blood serum. The chemical and the plastics material onto which it is to be adsorbed, or covalently bonded, have been brought into contact with one another manually, either by immersing a plastics solid form in a solution of the chemical; or by plastics-coating the inside of a tube-like container. The coated plastics form, or coated container, may then be used to determine the concentration of an analyte in a liquid sample by dipping or by filling. Each stage of such an analysis has required a manual transfer which is time consuming, imprecise, causes problems in maintaining patient identity, and is expensive. The present invention allows these disadvantages to be reduced through a partial mechanisation of the process. It is to be understood that the invention is not restricted in use to the chemical testing of samples, but may also be applied to physical tests.

According to the invention, apparatus for testing at least one liquid sample, by immersion therein of a probe for coaction between said probe and sample, has a reloadable sample carrier for at least one sample container; a reloadable probe carrier for at least one probe; a frame having locating means for relatively locating the sample carrier and the probe carrier laterally in the frame, parallel motion means for guiding the probe longitudinally into the sample container and stop means for locating the probe at a predetermined distance into the sample container, locking means preventing the probe from being withdrawn more than a predetermined distance in the outward direction from the sample container, timing and control means for releasing said locking means after a predetermined time, and self acting withdrawal means for withdrawing the probe and probe carrier to a position clear of the sample container; the said sample carrier and probe carrier being arranged so as to be severally removable away from the said frame.

The apparatus may be arranged for a plurality of probes and samples for coaction simultaneously.

The stop means and locking means may include an electromagnet and an armature therefor; and the timing and control means are conveniently actuated through switch means by longitudinal relative movement of the probe carrier and sample carrier.

The self-acting withdrawal means conveniently includes a spring, aiding withdrawal; and preferably also includes damper means, which may be an air dash pot.

The sample carrier may be arranged to be heatable electrically and thermostatically by a heating element and temperature sensitive element therein; and the heating element may be arranged to be connectable to an energy source only when the sample carrier is put into the frame so it can register with a probe carrier.

The probe carrier is preferably formed so it can be placed on a flat surface without any probe being dislodged from it and so that the probe does not touch the surface.

Oscillating means may be included in the apparatus which can oscillate the probe carrier longitudinally through a small distance in relation to the sample carrier whereby a probe may be moved in an oscillatory manner in relation to a sample in a sample container.

The apparatus may be arranged so that the frame has a plurality of locations, each for a set of probe carrier and sample carrier, which are then preferably formed each with characteristic mutually associable portions, whereby a given one of the plurality of locations in the frame can be occupied only by an individual probe carrier and an individual corresponding sample carrier. In one embodiment the associable portions are interlocking portions interlocking through direct translatory movement between frame and probe carrier and between frame and sample carrier.

BRIEF DESCRIPTION OF THE ACCOMPANYING DRAWINGS

The invention will be further described, by way of example, with reference to the accompanying drawings, in which FIGS. 1a and 1b is an elevation of a testing apparatus.

DETAILED DESCRIPTION OF THE PREFERRED EXEMPLARY EMBODIMENT

Figure 1B:
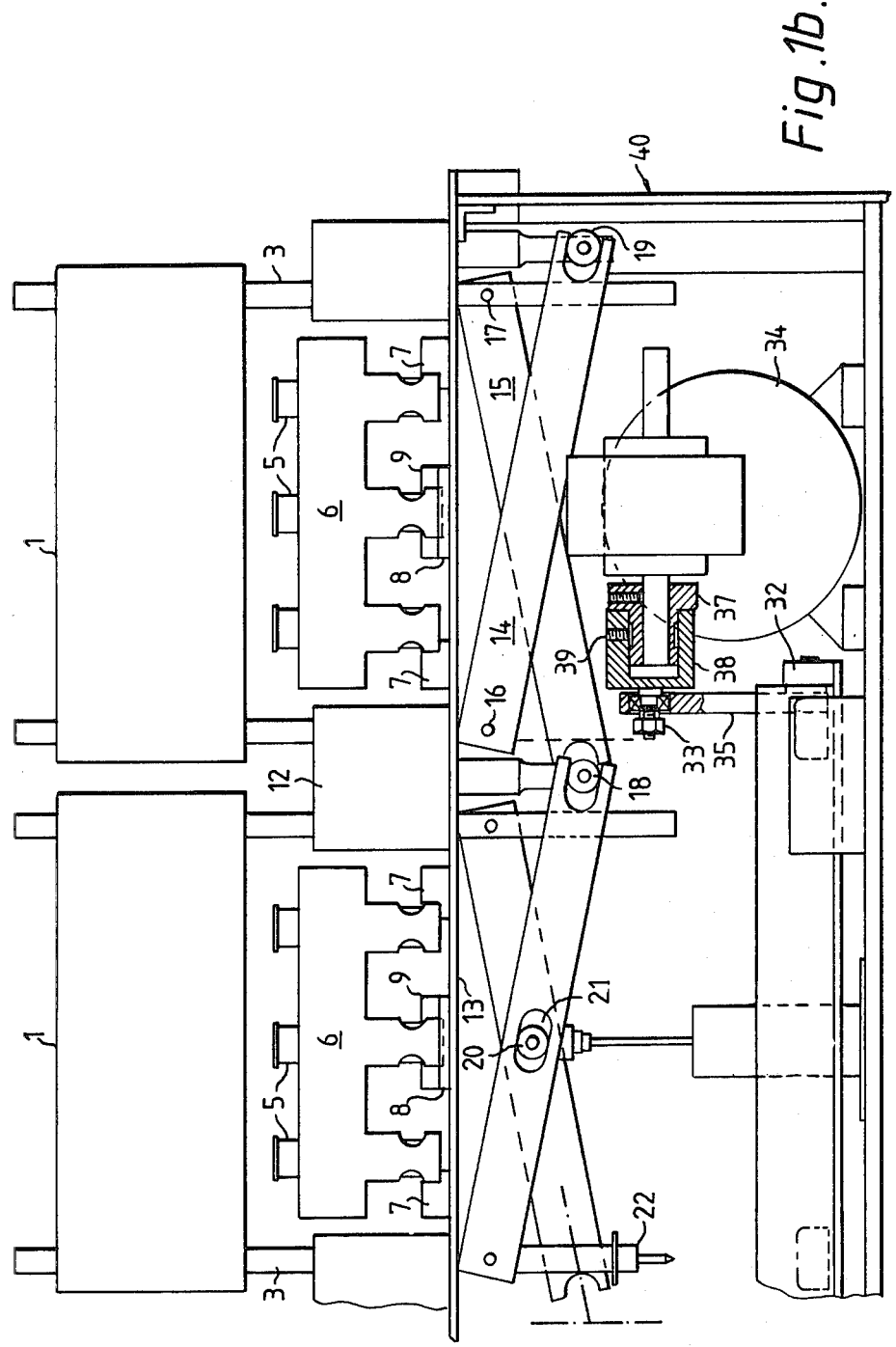

Referring to FIG. 1, the apparatus comprises a frame, indicated generally by reference number 40, having four similar locations into which can be loaded a probe carrier 1 and a sample carrier 6. The probe carrier is in the form of a plate supporting probes 2. Here the probes are solid plastics forms in the shape of flags. Alternatives to the flag form are cylinders or spheres, which may be made hollow of cellular if required.

The probe carrier is placed manually in the frame on rods 3 and is constrained in the vertical direction by support blocks 4. Thus an array of probes or flags 2 is positioned in register over a corresponding array of sample containers 5 which are supported in a thermostatically temperature controlled block 6 ie the sample carrier. The block 6 is manually inserted into the frame 40 and is accurately positioned by guides 7 and end stops 8 and 9. Inserting the block 6 causes a heating element therein to be connected by plug and socket means to a source of electrical energy. The rods 3 are guided vertically by bearings 11 in blocks 12, supported by a top plate 13 of the frame 40. The lower parts of the rods 3 are connected together by levers 14 and 15. These are pivoted at rods 3 at positions 16 and 17 at one end of each lever respectively. The other end of each lever is guided by a rotatable sliding ball bearing joint at 18 and 19 respectively. A ball bearing 20 is fitted onto a shaft extending from the side face of lever 15 which engages in the slot 21 machined centrally in lever 14. It will be appreciated that this system of levers forms a parallel motion to guide rods 3 to prevent any possibility of jamming when the probe carrier 1 moves up or down.

In operation the probe carrier 1, in position on rods 3, is pressed down manually. This causes the probes 2 to be immersed in any chemical contained in the sample containers 5. The probe carrier is stopped and held in the down position through rods 3 and levers 14,15, by the armature 22 meeting and being held by electro magnet 23.

Figure 2A:
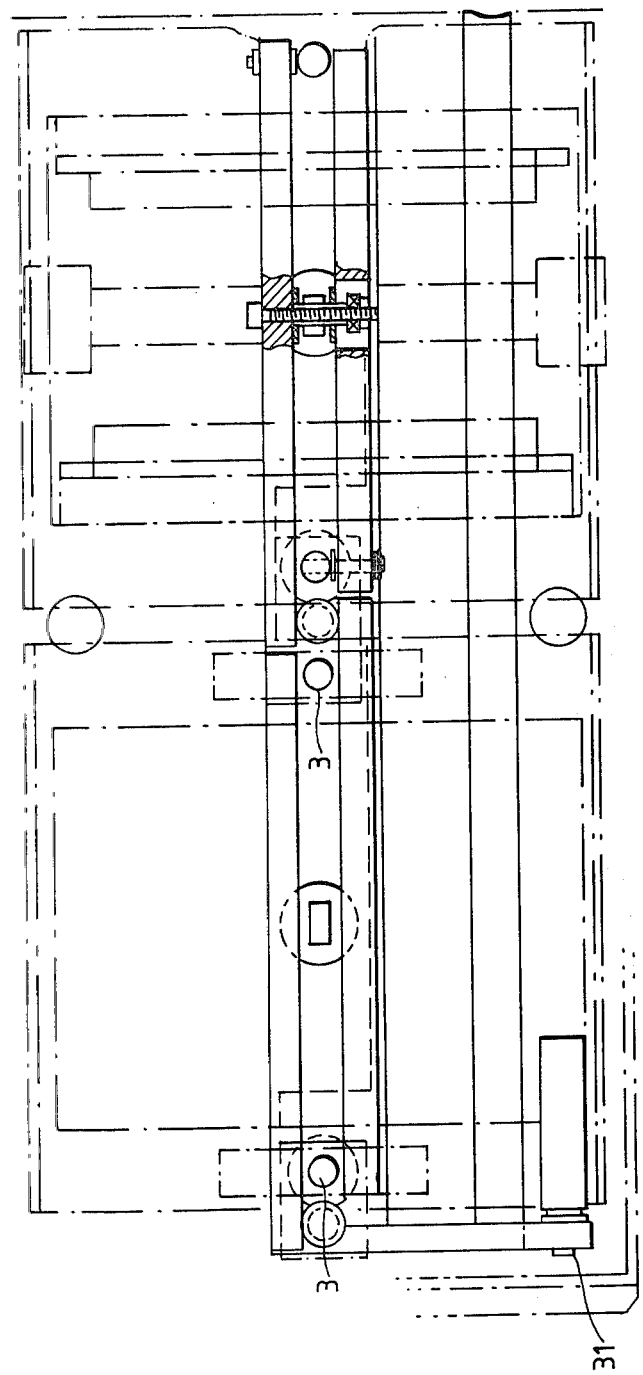
FIGS. 2a and 2b is a plan corresponding to FIG. 1.
Figure 2B:
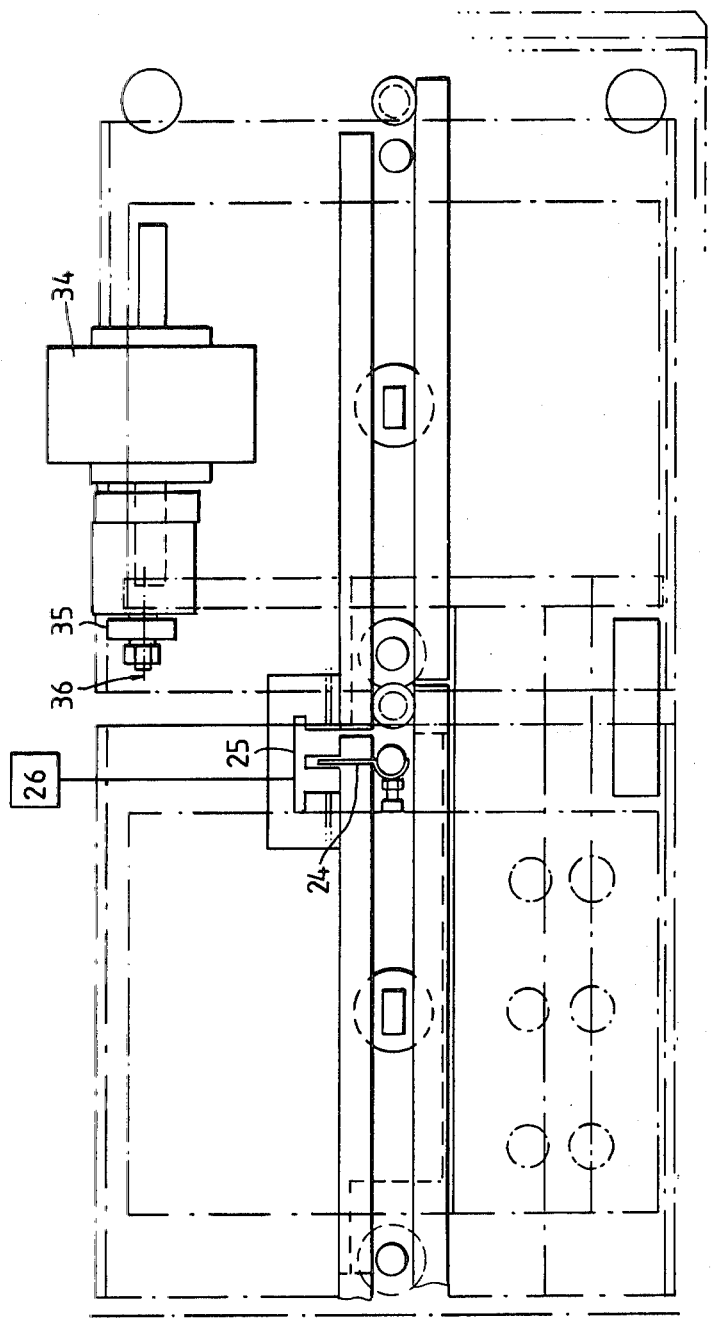

Current to the electromagnet is switched on by the vane 24 interrupting the optic path of photoelectric switch means 25. The time the probes 2 remain in the chemicals in sample conteiners 5 is automatically initiated by the action of pressing down plate 1 to actuate switch means 25. The time may be selected manually through an adjustable timer indicated diagrammatically at 26 (FIG. 2). Upon release of the armature 22 at the end of the selected time, the rods 3 are caused to ascend by spring 27, the velocity being controlled by an air dash pot 28. The degree of damping may be selected manually by adjustment of a bleed screw 29.

With the probe carrier 1 in the down position, the probes 2 may be caused to oscillate a small distance vertically so as to cause agitation of liquid in the sample containers 5. The amount of oscillation has been found to be usefully about ±1 mm at 680 cycles/min with approximately sinusoidal motion. This is achieved by mounting the electromagnet 23, for each location in frame 40, on a platform 30 which is pivoted in the frame 40 at 31 and 32. An eccentric pin 33 capable of being revolved by motor 34 is connected by a link 35 to platform 30 at pivot point 36, thus the platform is made to oscillate. The degree of eccentricity of the pin 33 may be manually set by rotating the two eccentrics 37 and 38 relative to each other and then locking by screw 39. The frequency of oscillation may be controlled by varying the speed of the motor 34, using conventional speed control means.

The apparatus may be provided with a transparent hinged cover to prevent draughts of air affecting the temperature at which chemical reactions take place in the sample containers.

The probe carrier 1 is formed from sheet metal with folded down ends at 1a and 1b. These form supports so that the probes 2 are protected when the carrier 1 is placed on a flat working surface. A second function of the ends 1a and 1b is to ensure that if the sample carrier 6 is not correctly positioned in the apparatus the probes 2 cannot be lowered. A third function is to overlap the sample carrier 6 and prevent it from being withdrawn from the frame 40 when probes 2 are in the sample containers 5.

Figure 3:
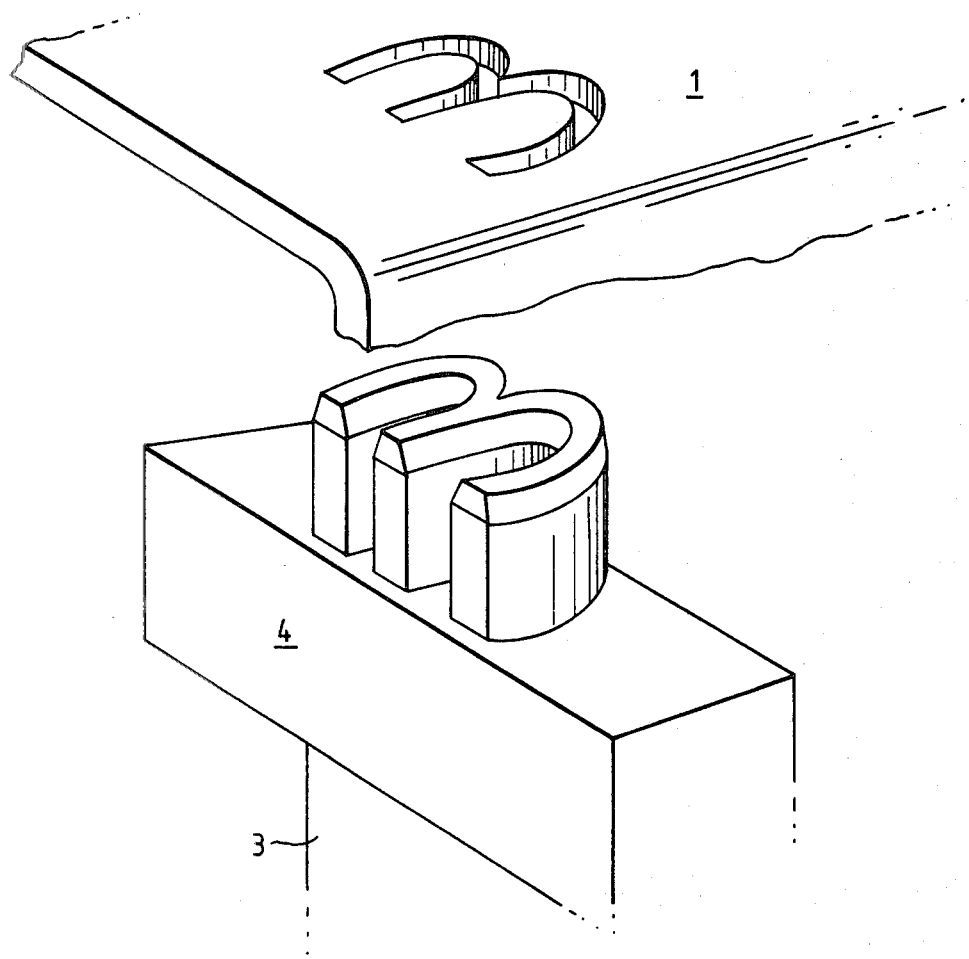
FIG. 3 is a detail trimetric view of interlocking portions of frame and probe carrier.

FIG. 3 shows a means of unequivocally associating a probe carrier 1 with a particular sample carrier 6. This is important in maintaining the identity of the sample being analysed. it will be seen in FIG. 3 that rods 3 are terminated at the upper end in a portion shaped like a three dimensional number three.

A corresponding female portion is formed in probe carrier 1. Thus "number three" probe carrier can only be inserted in "number three" position in frame 40. Similarly the sample carrier 6 has the same number, on the face thereof to be first inserted in the frame 40. Male and female forms of the number three may be arranged in the plug and socket connecting the sample carrier to a source of electrical energy. Each location in the frame 40 is, of course, allotted to a number different from the rest.

In the four locations in frame 40 for conducting analysis, each is conveniently provided with an individual timer 26; but all may share the same oscillating mechanism.

The means already described, and indicated in FIG. 3 of the drawings, for associating a probe carrier and a sample carrier unequivocally with a particular location in the apparatus is convenient and simple. Alternatives may, however, be used; for example interlocking arrays of pegs and holes, an electrical code-reading device, matching colour patterns, or a number association system.

The invention has been described in relation to probes which comprise solid plastics forms, eg of polystyrene, onto which substances such as antibodies may be bonded covalently, or in which they may be held. The probes are inserted into sample containers containing other chemicals, or internally coated with other chemicals (or both containing and coated), for a predetermined chemical reaction time, commencing at the same instant for all samples at a given location in the apparatus. At the end of the reaction time the probes are simultaneously and automatically removed from the sample containers.

However, the use of the invention is not restricted to probes of the kind already described. It may equally well be used with probes adapted for making pH, conductometric or colorimetric tests (for example) on liquid samples; or probes may be optically activated to measure or change the composition of a chemical in a sample container.

We claim:

1. Apparatus for testing at least one liquid sample, by immersion therein of a probe for coaction between said probe and sample, having a reloadable sample carrier for at least one sample container; a reloadable probe carrier for at least one probe; a frame having locating means for relatively locating the sample carrier and the probe carrier laterally in the frame; parallel motion means for guiding the probe longitudinally into the sample container and stop means for locating the probe at a predetermined distance into the sample container; locking means preventing the probe from being withdrawn more than a predetermined distance in the outward direction from the sample container; timing and control means for releasing said locking means after a predetermined time; self-acting withdrawal means for withdrawing the probe and probe carrier to a position clear of the sample container; the said sample carrier and probe carrier being arranged so as to be severally removable away from said frame; and oscillating means which can oscillate the probe carrier longitudinally through a small distance in relation to the sample carrier; whereby the probe may be moved in an oscillatory manner in relation to a sample in a sample container.

2. Apparatus according to claim 1 arranged for a plurality of probes and samples for coaction simultaneously.

3. Apparatus according to claim 1 in which the stop means and locking means include an electromagnet and an armature therefor.

4. Apparatus according to claim 1 in which the timing and control means are actuated through switch means by longitudinal relative movement of the probe carrier and the sample carrier.

5. Apparatus according to claim 1 in which the self-acting withdrawal means includes a spring arranged so as to aid withdrawal.

6. Apparatus according to claim 1 in which the self-acting withdrawal means includes damper means.

7. Apparatus according to claim 6 in which the damper means is an air dash pot.

8. Apparatus according to claim 1 in which the sample carrier is heatable electrically and thermostatically.

9. Apparatus according to claim 8 in which an electrical heating element is arranged to be connectable to an energy source only when the sample carrier is put into the frame so it can register with a probe carrier.

10. Apparatus according to claim 1 in which the probe carrier is so formed that in use it can be placed on a flat surface without any probe being dislodged from said carrier and so that no probe touches said flat surface.

11. Apparatus according to claim 1 in which the frame has a plurality of locations, each for a set of probe carrier and sample carrier.

12. Apparatus according to claim 11 in which each said location and a set of probe carrier and sample carrier are all formed with characteristic mutually associable portions whereby a given one of the plurality of locations in the frame can be occupied only by an individual probe carrier and an individual corresponding sample carrier.

13. Apparatus according to claim 12 in which the associable portions are interlocking portions interlocking through direct translatory movement between frame and probe carrier and between frame and sample carrier.

14. Apparatus for testing at least one liquid sample, by immersion therein of a probe for coaction between said probe and sample, having a reloadable sample carrier for at least one sample container; a reloadable probe carrier for at least one probe; a frame having a plurality of locations each for a set of probe and sample carriers and including locating means for relatively locating a set of sample carrier and probe carrier laterally in the frame; parallel motion means for guiding the probe longitudinally into the sample container and stop means for locating the probe at a predetermined distance into the sample container; locking means preventing the probe from being withdrawn more than a predetermined distance in the outward direction from the sample container; timing and control means for releasing said locking means after a predetermined time; and self acting withdrawal means for withdrawing the probe and probe carrier to a position clear of the sample container; and wherein each set of probe carrier and sample carrier are all formed with characteristic mutually associable portions whereby a given one of the plurality of locations in the frame can be occupied only by an individual probe carrier and an individual corresponding sample carrier.

15. Apparatus according to claim 14 in which the associable portions are interlocking portions interlocking through direct translatory movement between frame and probe carrier and between frame and sample carrier.

* * * * *